United States Patent [19]

Dietsche

[11] 4,029,657

[45] June 14, 1977

[54] 6,7-DICHLORO-3,4-DIHYDRO-2H-PYRAZINO(2,3-B)(1,4)OXAZINES

[75] Inventor: Thomas J. Dietsche, Berkeley, Calif.

[73] Assignee: The Dow Chemical Company, Midland, Mich.

[22] Filed: June 14, 1976

[21] Appl. No.: 695,711

[52] U.S. Cl. .................. 260/244 R; 424/250
[51] Int. Cl.² ........... C07D 265/00; C07D 273/00; C07D 295/00; A01N 9/00
[58] Field of Search .................. 260/244; 424/250

[56] References Cited
UNITED STATES PATENTS 3,274,191  9/1966  Gragoe et al. .................. 260/244 R Primary Examiner—Albert T. Meyers
Assistant Examiner—D. W. Robinson
Attorney, Agent, or Firm—Robert R. Stringham

[57] ABSTRACT

Dichloropyrazino-oxazines of the formula

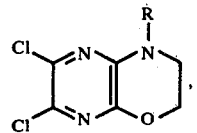

wherein R is H or a $C_1$ to $C_8$ alkyl, alkenyl, cycloalkyl or cycloalkenyl radical, are disclosed. The compound in which R is H has utility as an intermediate for the compounds in which R is other than H. The latter compounds exhibit microbicidal, herbicidal or insecticidal activity. The compounds of the invention are readily prepared from tetrachloropyrazine and 2-aminoethanols of the formula R—NH—CH$_2$CH$_2$—OH.

10 Claims, No Drawings

6,7-DICHLORO-3,4-DIHYDRO-2H-PYRAZINO(2,3-B)(1,4)OXAZINES

BACKGROUND OF THE INVENTION

No disclosure of a halogen substituted pyrazino-oxazine has been found in the literature. Hexahydro-2'-methylspiro(cyclohexane-1,8'(6H)-oxazino(3,4-A)pyrazine) is included in a list of compounds reported by G. Chen, Proc. Soc. Expt. Biol. Chem., 112, 611 (1963) to have been examined for convulsant properties, this is the closest known prior art compound to the pyrazino-oxazines of the present invention.

SUMMARY OF THE DESCRIPTION

The present invention is a group of substituted 6,7-dichloro-3,4-dihydro-2H-pyrazino(2,3-b)(1,4) oxazine compounds (hereinafter referred to as "pyrazino-oxazine" compounds) having utility as intermediates, microbicides, herbicides or insecticides. They are of the formula

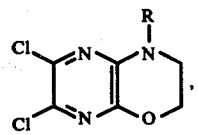

wherein R is H, alkyl of 1-8 carbons, alkenyl of 2-8 carbons, cycloalkyl of 3-8 carbons or a cycloalkenyl radical of 4 to 8 carbons.

The foregoing compounds are prepared by reacting tetrachloropyrazine with a 2-aminoethanol of the formula $RNHCH_2CH_2OH$, wherein R has the meaning given above, in the presence of a hydrogen chloride acceptor to form a compound of the formula

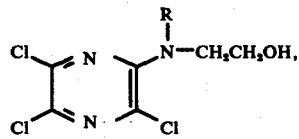

which is then cyclized by reaction with a base, such as KOH or $NaO.C_2H_5$.

Alternatively, the tetrachloropyrazine can be converted in a single operation to the desired pyrazino-oxazine by reacting it with the 2-aminoethanol in the presence of a base (such as the above) which is capable of converting the aminoethanol to a salt, such as $RNH-CH_2CH_2O^-$, $Na^+$.

DETAILED DESCRIPTION OF THE INVENTION

The pyrazino-oxazines of the present invention are white to tan solids or oils which, with the exception of the compound in which R is H, are generally soluble in common organic solvents. More powerful solvents, such as dimethyl formamide (DMF), tetrahydrofuran, dimethylsulfoxide (DMSO), dioxane or hexamethyl phosphoramide (HMPA) are required to dissolve substantial amounts of the latter compound.

Typical aliphatic and cycloaliphatic radicals represented by R in the above formulas include methyl, isopropyl, allyl, cyclopentyl, n-hexyl, t-butyl, crotyl, cyclohexenyl, iso-octyl and the like. The corresponding amino-ethanols are known or can be prepared by known methods, such as, for example, the reaction of a primary amine with ethylene oxide (see Method 442; Wagner and Zook, Synthetic Organic Chemistry; P. 672 (1953), Wiley).

Tetrachloropyrazine is a known compound which can be prepared by vapor phase chlorination of pyrazine. See U.S. Pat. No. 3,420,833.

From the standpoint of versatility as an intermediate, the compound of the invention in which R is H is preferred.

From the standpoint of biological activity, those compounds of the invention in which R is other than H are preferred. Among these, the compounds in which R is a non-cyclic (alkyl or alkenyl) radical, particularly a radical of 3 to 5 carbons — are preferred, as having greater biological activity. The compound in which R is n-butyl is particularly preferred, by reason of its greater activity as a microbicide.

Among the compounds in which R is a cycloalkyl or -alkylene radical, those in which said radical is of from 5 to 7 carbons are preferred for reasons of availability or cost of the requisite starting materials.

The compounds of the present invention may be prepared by either of the procedures summarized above. Compounds of the invention in which R is other than H may also be prepared, by resort to known N-alkylation procedures, from the compound in which R is H.

When tetrachloropyrazine is first reacted with the aminoethanol in the presence of a hydrogen chloride acceptor, a solvent may or may not be employed, depending on such factors as the liquidity of the mixed reactants in the absence of a solvent or the influence of a solvent on subsequent ease of separation of the desired product from by-products such as triethylamine hydrochloride (triethylamine being used as the hydrogen chloride acceptor).

Substantially elevated temperatures are generally not required for the tetrachloropyrazine/aminoethanol reaction. The reaction usually proceeds at a satisfactory rate at room temperature but may be speeded up by carrying it out at the reflux temperature of a relatively low boiling solvent, such as tetrahydrofuran (THF) or benzene.

The reactant ratio is not critical, since some of the desired intermediate product will form at any ratio. However, it is preferred to use stoichiometric amounts of the tetrachloropyrazine and the aminoethanol and at least a stoichiometric proportion of the hydrogen chloride acceptor.

The hydrogen chloride acceptor can be any material which does not unduly interfere with formation or recovery of the desired product and which will effectively maintain the hydrogen chloride activity in the reaction mixture at a negligible level. A convenient material for this purpose is a soluble base, such as triethylamine, but other bases or other types of hydrogen chloride scavengers may be used.

Somewhat higher temperatures are generally used in the subsequent ring closure step. Suitable temperatures range from about normal room temperatures up to about the reflux temperature of dioxane (~101°) at 760 nm. For this step, a solvent will usually be employed as a medium for the reaction and water may be used as a co-solvent where necessary to ensure an adequate degree of base dissolution. Again, reactant ratios are not critical but stoichiometric amounts of the reactants preferably are employed.

In both steps, suitable contact times range from a few hours to 24 hours or more, depending upon such factors as the solubility of the HCl scavenger or base employed, the activities of the reactants in the mixture and the temperature. The progress of the reaction, in either step, of course may be followed by withdrawing and analyzing samples of the reaction mixture.

Work-up procedures such as ordinarily are employed for reactions of the type involved are satisfactory in the present preparative method.

The compound of the invention in which R is H has been found to be insecticidally active against cabbage looper but would generally be uneconomic to use for control of this pest. However, it is of value as an intermediate for the preparation of other compounds of the invention, particularly those which require more expensive or difficult-to-prepare aminoethanols as starting materials in the preceding methods of preparation.

When the >N—H compound is employed as intermediate, it is first converted to a corresponding alkali metal salt by reaction with a base, such as potassium t-butoxide, sodium hydride or sodium ethoxide in an appropriate solvent, such as THF, DMF or the dimethyl ether of ethylene glycol. The salt is then reacted in-situ with an appropriate alkyl, cycloalkyl, alkenyl or cycloalkenyl chloride or bromide. Alternatively, the >N—H compound may be converted to the corresponding N—Si—($CH_3$)$_3$ compound (by reaction with trimethyl chlorosilane), which is then reacted with aliphatic or cyclo-aliphatic halide to give the corresponding trimethylhalosilane and the desired >N—R compound of the invention. Reaction conditions, contact times and work-up procedures conventionally employed for such reactions are suitable.

The following examples are for purposes of illustration and are not to be construed as limiting the present invention to a scope other than as set forth in the claims in this application.

EXAMPLES

A. Syntheses

EXAMPLE 1

2-(Methyl(trichloropyrazinyl)amino)-ethanol

A mixture of tetrachloropyrazine (10.8g, 0.05 mol), methylaminoethanol (3.7g, 0.05 mol), and triethylamine (10g, 0.1 mol) was stirred overnight at room temperature. The white solid was filtered out and the filtrate concentrated on the rotary evaporator to leave a yellow oil. This was distilled on a Kugelrohr apparatus to give 10g (78% of theoretical yield) of a yellow oil (b.p. 110° at 0.05 mm Hg).

Anal. Calcd. for $C_7H_8Cl_3N_3O$: C, 32.78; H, 3.14; Cl, 41.46; N, 16.38. Found: C, 32.71; H, 3.45; Cl, 41.85; N, 15.96.

EXAMPLE 2

6,7-Dichloro-3,4-dihydro-4-methyl-2H-pyrazino(2,3-b)(1,4)oxazine

The crude product from the reaction of tetrachloropyrazine (10.8g, 0.05 mol) and methylaminoethanol (3.7g, 0.05 mol) in Example 1 above was dissolved in absolute ethanol and small pieces of sodium (1.2g, 0.05 mol) were added. After stirring overnight the ethanol was evaporated and the solid residue was washed with water, filtered, and dried on a porous plate to a weight of 7g. The solid was recrystallized from ethanol and isopropyl alcohol (IPA) to give 4g (27% yield) of a white solid, m.p. 170°–2°.

Anal. Calcd. for $C_7H_7Cl_2N_3O$: C, 38.21; H, 3.21; N, 19.10. Found: C, 38.25; H, 3.44; N, 19.24.

EXAMPLE 3

6,7-Dichloro-3,4-dihydro-2H-pyrazino(2,3-b)(1,4)oxazine (2-Hydroxyethylamino)-trichloropyrazine (12.1g, 0.05 mol) and crushed KOH (5g, 85% assay, 0.075 mol) were contacted in refluxing benzene overnight. The solid phase was filtered out and stirred in water, $CH_2Cl_2$, and IPA and refiltered after each wash to give 3g (30% yield) of an off-white solid.

Anal. Calcd. for $C_6H_5Cl_2N_3O$: C, 34.98; H, 2.45; N, 20.40. Found: C, 34.33; H, 2.93; N, 19.71.

EXAMPLE 4

4-Butyl-6,7-dichloro-2,3-dihydro-pyrazino(2,3-b)(1,4)oxazine

A mixture of tetrachloropyrazine (21.8g, 0.1 mol), n-butylaminoethanol (11.7g, 0.1 mol), and potassium carbonate (28g, 0.2 mol) were heated to 80° in 225 ml of dioxane and 50 ml of water for 24 hours. After extraction with $CH_2Cl_2$ and concentration with rotary evaporation, 30g of an oil characterized by nmr as the N-substituted product was obtained. An attempt to distill 5g of this material led to decomposition. The rest of the material was dissolved in 200 ml of benzene and refluxed for 2 hours with crushed KOH (10g, 85% assay, 0.15 mol). The mixture was partitioned between water and $CH_2Cl_2$. The organic layer was dried ($MgSO_4$) and rotary evaporated to give a crude oil. This was distilled two times on a Kugelrohr apparatus (b.p. about 130° at 0.5 mm Hg) to give 12.5 g (48% yield) of the title product.

Anal. Calcd. for $C_{10}H_{13}Cl_2N_3O$: C, 45.82; H, 5.00; N, 16.03. Found: C, 45.40; H, 4.33; N, 15.86.

EXAMPLE 5

6,7-Dichloro-4-ethyl-3,4-dihydro-2H-pyrazino(2,3-b)(1,4)oxazine

Tetrachloropyrazine (22g, 0.1 mol), ethylaminoethanol (9g, 0.1 mol), and crushed KOH (16.5g, 85% assay, 0.25 mol) were contacted overnight in 200 ml of refluxing benzene. Work-up gave a mixture of the oxazine (25%) and of the O-adduct (75%). The mixture was dissolved in THF and triethylamine (20g, 0.2 mol) was added and held at reflux temperature for 6 days. The solid was filtered, the THF rotary evaporated, and the residual oil was partitioned between water and $CH_2Cl_2$. The organic layer was dried ($MgSO_4$) and rotary evaporated to leave an oily residue. This was recrystallized from hexane and IPA to give two crops totaling 2.8g (12% yield), m.p. 108°–10°.

Anal. Calcd. for $C_8H_9Cl_2N_3O$: C, 41.05; H, 3.88; N, 17.95. Found: C, 40.95; H, 3.84; N, 17.70.

B. Biological Activity

EXAMPLE 6

The following compounds of the invention were tested for microbicidal, herbicidal or insecticidal activity by one or more of the procedures below:

| compound | R |
|---|---|
| a. | Methyl |
| b. | Ethyl |
| c. | n-Butyl |

Tests for microbicidal (including fungicidal) activity.

1. Application of Chemicals to Leaves to Prevent Foliar Diseases

Host plants are wet with an aqueous solution or suspension of the experimental chemical. The concentration of chemical usually ranges from 600 ppm down. Acetone or isopropanol and wetting agents are usually both added to the composition to give better dissolving and wetting characteristics. After the chemical has been applied the plants are inoculated with the pathogen. They are then stored in conditions suitable for infection and development of the diseases. When symptoms are well developed the plants are graded for disease control. The untreated checks are rated as no control and the absence of disease symptoms as 100% control.

2. An In Vitro Agar Petri Dish Dilution Test for Determining Bacteriocidal and Fungicidal Activity of Chemicals Chemicals are diluted in isopropanol or other appropriate solvents. They are then diluted to desired concentration in warm melted agar, poured into petri dishes, and the agar allowed to solidify.

Droplets of the test organism are applied to the surface of the agar with an "Accu Drop" (The Sylvania Co., Orange, N.J.). Plates are incubated at an appropriate temperature for a suitable time and read. Percent activity is noted.

3. Combination of Root Drench and Foliar Treatment for Control of Foliar Diseases, In Vivo Chemicals are applied to foliage as described in procedure No. 1. The pots are then either placed into cups containing solutions of the chemicals or else the chemicals are drenched into the pots. The plants are then inoculated with the disease, usually 24 hours following treatment.

4. Pre-Emergence Herbicide

As a pre-emergence herbicide test, pots are filled to within 1 inch of the top with a medium-textured soil and seeds of any species considered appropriate (such as pigweed, field bindweed, velvetleaf, cotton, barnyardgrass, foxtail, wild oat and crabgrass) are sown in their appropriate area. The seeds are then covered with a ½-inch layer of a sandy soil and test chemicals formulated at the desired concentration are drenched onto the soil surface in sufficient volume to wet the top 1½ to 2 inches of soil. The pots are maintained in the greenhouse and are top-watered as necessary. Final readings are made about 2 weeks after treatment, the exact time depending upon the rate of plant growth. Readings are based on the germination and the growth of treated plants compared with that of untreated plants. Readings of 0 = no visible effects and 100 = all plants dead.

5. Post-Emergence Herbicide

As a post-emergence herbicide test, pots are filled with a sandy soil, and plants of any species considered appropriate (such as pigweed, field bindweed, velvetleaf, cotton, barnyardgrass, foxtail, wild oat, and crabgrass) are grown to an average height of 2 to 4 inches. Plants are then sprayed to run-off with an aqueous solution or dispersion containing the test chemical at the desired concentration. The plants are maintained in the greenhouse and are sub-irrigated as necessary. Final readings are made 2 weeks after treatment. Readings represent the percent kill or control of growth on the treated plants when compared to untreated plants, with 0 = no visible effects and 100 = all plants dead.

Tests for insecticidal activity.

6. Plant Insecticide: Systemic Soil Application

The test plants are grown singly in 3-inch pots. Plants are used before the primary leaves are fully expanded and before terminal growth occurs. Insects, either cultured or field collecting may be used as indicated. Injection of the test solution into the soil (vermiculite) at the base of the plant is made with a pistol-grip veterinary syringe with a large needle 4 inches long. A one-ounce plastic cup with a snap top may be used to contain armyworms and similar insects while being immersed.

Chemical application is made only by injection below the soil surface into the root zone. Any insecticidal effect on organisms feeding on the leaf or stem portion is presumed to be due to chemical uptake through the plant. This test may be used with any organism normally infesting the above ground plant parts. In the case of larvae requiring caging (as the beet armyworm) the plants are infested after soil treatment. When mites or aphids are used, the plant may be infested prior to soil injection. Mortality counts are made from 3 to 6 days after chemical treatment and corrected for natural mortality.

7. Insect Contact Spray

Paper cylindrical cartons, 3⅝ in diameter by 3¼ inch high fitted on the top and bottom with a metal screen are used for test cages. A counted number of insects are placed in each cage. An aqueous dispersion of the test compound is sprayed down, through the screen lid from a distance of approximately 15 inches using a Spraying Systems Company nozzle. The test insects may be fed sugar water for 3 days, then mortality counts are made. Knockdown counts may be recorded after the first hour.

| Compound | Test | Concentration | Organism | % Control |
|---|---|---|---|---|
| a. | 7 | 400 | German cockroach | 50 |
|  | 2 | 500 | Trichophton mentagrophytes | 50 |
| b. | 6 | 400 | 2-Spotted Spider Mite | 98 |
|  | 7 | " | German cockroach | 67 |
|  | 5 | 4000 | Pig weeds | 100 |
|  |  |  | Crabgrass | 40 |
|  | 1 | 400 | Downey mildew | 99 |
|  | 3 | " | Apple powdery mildew | 90 |
| c. | 4 | 10 lbs/acre | Pigweeds | 90 |
|  | 5 | 4000 ppm | Pigweeds | 100 |
|  |  |  | Crabgrass | 80 |

-continued

| Compound | Test | Concentration | Organism | % Control |
|---|---|---|---|---|
| 1 | | 400 | Downey mildew | 100 |
| | | 100 | | |
| | 2 | 500 | Trichophton mentagrophytes | 100 |
| | | | Rhizopus nigricans | 50 |
| | | | Trichoderm sp. | 50. |

What is claimed is:

1. A dichloropyrazino-oxazine of the formula:

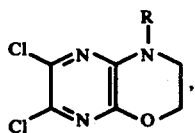

wherein R is H, alkyl of 1–8 carbons, alkenyl of 2–8 carbons, cycloalkyl of 3–8 carbons or a cycloalkenyl radical of 4 to 8 carbons.

2. The compound of claim 1 in which R is alkyl of 1–8 carbons, alkenyl of 2–8 carbons or cycloalkenyl of 4–8 carbons.

3. The compound of claim 2 in which R is alkyl of 1–8 carbons or alkenyl of 2–8 carbons.

4. The compound of claim 2 in which R is a cyclic radical of from 5 to 7 carbons.

5. The compound of claim 3 in which R is an alkyl or alkenyl radical of from 3 to 5 carbons.

6. The compound of claim 5 in which R is n-butyl.

7. The compound of claim 1 in which R is H.

8. The compound of claim 1 in which R is an alkyl group.

9. The compound of claim 8 wherein R is methyl.

10. The compound of claim 8 wherein R is ethyl.

* * * * *